United States Patent [19]

Jensen et al.

[11] Patent Number: 4,772,134
[45] Date of Patent: Sep. 20, 1988

[54] FLUID CONTAINER PORT CONNECTOR MOUNTING

[75] Inventors: Ole R. Jensen, River Vale, N.J.; Walter F. Leise, Yardley, Pa.; Frank M. Freeman, Lawrenceville, N.J.

[73] Assignee: E. R. Squibb & Sons, Princeton, N.J.

[21] Appl. No.: 17,895

[22] Filed: Feb. 24, 1987

[51] Int. Cl.⁴ ............................................. B65D 30/00
[52] U.S. Cl. .................................... 383/127; 383/904; 383/906; 285/382.4; 220/76
[58] Field of Search ........................ 383/127, 904, 906; 220/75, 76; 285/302, 330, 334.3, 382.4, 400, DIG. 22

[56] References Cited

U.S. PATENT DOCUMENTS

| | | | |
|---|---|---|---|
| 3,122,297 | 2/1964 | Sachs | 383/904 |
| 4,641,362 | 2/1987 | Muller | 383/904 |
| 4,645,247 | 2/1987 | Ward | 285/382.4 |
| 4,650,452 | 3/1987 | Jensen | 383/904 |
| 4,707,389 | 11/1987 | Ward | 383/904 |

*Primary Examiner*—Willis Little
*Attorney, Agent, or Firm*—James & Franklin

[57] ABSTRACT

The container has an elongated port section formed of a flexible cylindrical wall. A first tube member is lodged within the wall at a location spaced from the end thereof. A second tube member is forceably inserted within the first tube member, engaging a section of the wall therebetween. The engaged wall section may include a double wall thickness. One of the tube members is composed of substantially non-elastic material and the other is composed of relatively elastic material. The elastic member will deform so as to tightly seal the wall section. A detent may be present on one of the tube members to cooperate with a detent receiving recess on the other to enhance the strength of the seal. Any conventional drain valve or tubing can be connected to the protruding end of the second tube member.

21 Claims, 6 Drawing Sheets

FLUID CONTAINER PORT CONNECTOR MOUNTING

The present invention relates to fluid containers designed for medical applications and, more particularly, to a container port structure and a method for mounting a tube connector to the port of a flexible plastic pouch or bag such as a urostomy pouch or a collection receptacle of a urinary incontinence system.

Flexible pouches, bags or receptacles designed for use for medical purposes include ports which permit fluids to enter and/or exit. For example, urinary incontinence systems utilize collection receptacles in the form of plastic pouches or bags. In some cases, the pouches are provided with an inlet port connected to flexible tubing and/or an outlet port connected to a valve to permit drainage of the collected fluid. Drainage. valves of various types, employing clamps, the bending or kinking of a flexible tube, plugs, rotatable valves, and the like, have been utilized for this purpose. Regardless of the type of valve or tube, it is necessary to connect same to the container port in a manner which will be completely fluid-tight and, at the same time, strong enough to withstand the physical stresses to which the container will be subjected.

Virtually every type of flexible tubing or valve is easily connectable to a semi-rigid or rigid tube type connector having the appropriate connecting structure, such as screw threads, bayonet protrusions, annular protrusions, or the like. Therefore, the problem of connecting flexible tubing or drain valves to container ports can be solved by affixing a tube connector to the container port. Various methods of affixing such tube connectors to container ports have been attempted, including welding or adhesively sealing the container wall around the exterior of the tube connector. However, welding and adhesive sealing operations of sufficient accuracy to insure a fluid-tight seal require costly equipment and lack reliability.

The present invention relates to a simple way of using the natural resiliency of the components to obtain a fluid-tight, physically strong seal between a tube connector and a flexible container wall, without depending upon accurate welding or complete sealing by adhesive. A very high reliability seal can be obtained without utilizing specialized or costly production equipment.

It is, therefore, a prime object of the present invention to provide a fluid container port connector mounting which achieves a reliable, fluid-tight seal between the connector and the container port.

It is another object of the present invention to provide a fluid container port connector mounting which does not depend on accurate welding or complete adhesive sealing.

It is another object of the present invention to provide a fluid container port connector mounting which is simple in structure and does not require expensive or specialized equipment.

It is another object of the present invention to provide a fluid container port connector mounting which is inexpensive and reliable.

In accordance with one aspect of the present invention, a fluid container is provided comprising a reservoir portion and a port portion with a generally cylindrical flexible wall. First tubular means are situated within the wall at a location spaced from the end thereof. The first tubular means has an outer diameter substantially equal to the inner diameter of the wall. Second tubular means are inserted within the wall at the end thereof. One of the tubular means is composed of substantially non-elastic material and the other is composed of relatively elastic material. A portion of the second tubular means is inserted within the first tubular means slightly deforming the elastic one of the tubular means. A section of the wall is sealingly engaged between the exterior surface of the second tubular means and the interior surface of the first tubular means.

In one embodiment, the engaged wall section comprises first and second portions situated in side-by-side relation. One of the portions may be affixed to the exterior surface of the second tubular means either by welding or adhesive sealing.

The non-elastic tubular means perferably comprises a relatively rigid plastic tube. The elastic tubular means preferably comprises a relatively soft plastic tube.

Detent means are preferably provided on one of the tubular means. Detent receiving means are preferably provided on the other of the tubular means. The detent means preferably comprises annular protrusion means.

In accordance with another aspect of the present invention, a connector for mounting on a fluid container or the like is provided. The container is of the type having a reservoir portion and a port portion with a generally cylindrical flexible wall. The connector comprises a substantially non-elastic tube and a relatively elastic tube situated within the wall. One of the tubes is at least partially received within the other tube, deforming the elastic one of the tubes. The wall extends over the exterior surface of one tube and a section of the wall extends along the interior surface of the other tube. The section of the wall is sealingly engaged between the tubes.

The section comprises a first portion situated adjacent the interior surface of the one tube and a second portion situated adjacent the exterior surface of the other tube. The second portion is preferably affixed to the exterior surface of the other tube either by welding or by adhesive sealing.

The other tube preferably extends beyond the end of the one tube. In this way, it may extend into the interior of the reservoir portion of the container and form a sump.

Detent means may be provided on one of the tubes. Detent receiving means may be situated on the other of the tubes. Portions of the wall section are situated between the detent means and the detent receiving means.

The one tube is preferably relatively freely received within the wall. It is preferably not glued or welded within the wall.

In accordance with another aspect of the present invention, a method is provided for mounting a tubular connector member to the flexible wall of the portion of a fluid container or the like. The method comprises the steps of placing a tubular clamping member within the wall at a location spaced from the end thereof and placing the connector member within the wall proximate the end thereof. One of the members is substantially non-elastic and the other is relatively elastic. The connector member is inserted into the clamping member so as to deform the relatively elastic one of the members, thereby sealingly engaging a section of the wall between the interior surface of the connector member and the exterior surface of the clamping member.

The method further includes the step of affixing the exterior surface of the connector member to the wall prior to inserting the connector member into the clamping member. In this embodiment, the engaged wall section has two portions, one of which is affixed to the exterior surface of the connector member, and the other of which is situated adjacent the interior surface of the clamping member.

The clamping member is preferably composed of a heat shrinkable material or coated with a hot melt material. The method further comprises heating the clamping member subsequent to insertion of the connector member.

To these and to such other objects which may hereinafter appear, the present invention relates to a drainage valve connection for liquid containers as set forth in detail in the following specification and recited in the annexed claims, taken together with the accompanying drawings, wherein like numerals refer to like parts, and in which:

FIGS. 1 through 4 illustrate a first preferred embodiment of the present invention. Shown is the inlet or outlet port section of a fluid container such as a plastic bag or pouch, generally designated A. Pouch A has a fluid reservoir portion 10 and an elongated port section 12. Port section 12 is formed of a generally cylindrical wall made of relatively thin flexible material, such as plastic. Within wall 12 is placed a plastic tubular clamping member 14. The outer diameter of member 14 is substantially equal to or slightly greater than the inner diameter of wall 12. However, tubular member 14 is preferably not sealed to the interior of wall 12. It is either lightly or snugly received within wall 12 at a location spaced from the end 16 thereof.

Figure 1:
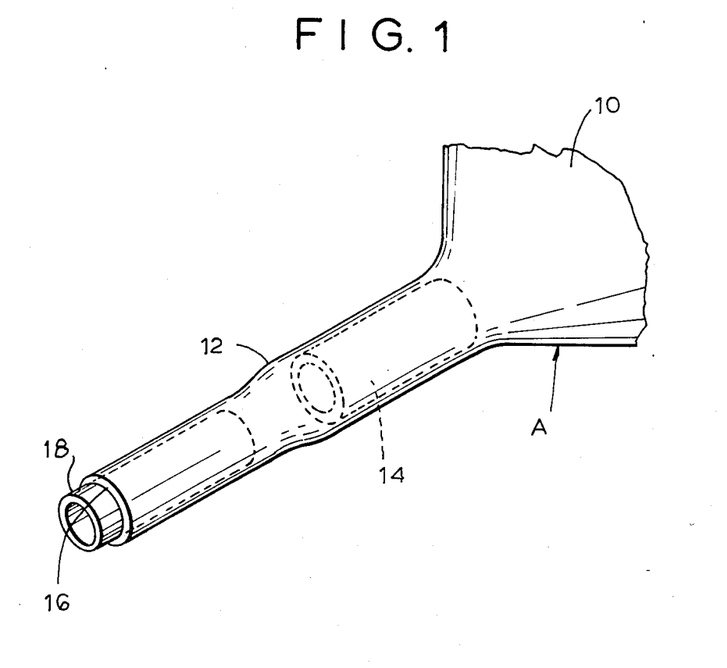
FIG. 1 is an isometric view of a first preferred form of the present invention prior to the insertion of the connector tube into the clamping tube.
Figure 2:
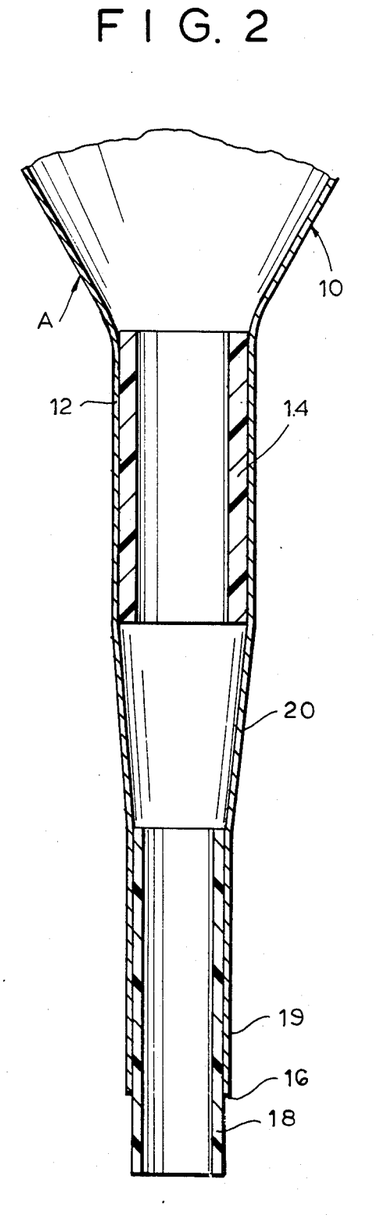
FIG. 2 is a side cross-sectional view of the embodiment of the present invention illustrated in FIG. 1.

Wall 12 preferably tapers to a smaller diameter proximate end 16. Within this tapered section is received a second tubular connector member 18 with a portion thereof extending beyond the end 16 of wall 12. The outer diameter of member 18 is preferably substantially equal to the inner diameter of member 14. The exterior surface of member 18 is preferably welded or sealed to the interior surface of section 19 of wall 12 by an adhesive sealant which remains flexible after curing, such as silicone.

One of the members 14 and 18 is composed of substantially non-elastic, preferably rigid hard plastic such as Nylon. The other of the members 14 and 18 is composed of a relatively elastic, preferably softer plastic such as polyethylene. In this way one of the members will deform to a small extent relative to the other when member 18 is inserted into member 14. If it is member 14 which is elastic, it will expand. If it is member 18 which is elastic, it will compress. This slight deformation will create a high clamping force between the members. If the polyethylene is used to form the connector member 18, it may be preferable to add ethyl vinyl alcohol to enhance its properties for welding to the pouch film. It is also preferable that the material of which clamping member 14 is composed be a heat shrinkable material or have an internal coating of a hot melt material. This will permit heating of the assembly to enhance the seal.

After tubular members 14 and 18 are in place, as shown in FIG. 2, member 18 is forceably inserted into the interior of member 14 such that a section 20 of wall 12 is captured or sealingly engaged between the wall section 19 and the interior surface of member 14. This causes the relatively elastic one of the tubular members to deform slightly and to create a relatively high force which tends to clamp the sections of wall 12 between the exterior surface of connector member 18 and the interior surface of clamping member 14, resulting in a fluid-tight friction seal. The seal is further enhanced by heating the assembly such that member 14 will shrink down or the interior layer thereof will melt, depending upon its composition.

Figure 3:
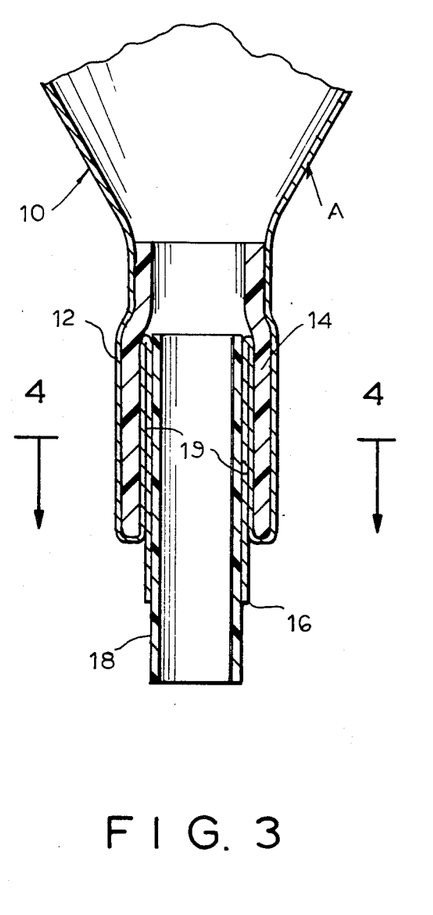
FIG. 3 is a side cross-sectional view of the embodiment of the invention illustrated in Fig. 2, shown after insertion of the connector tube into the clamping tube.
Figure 4:
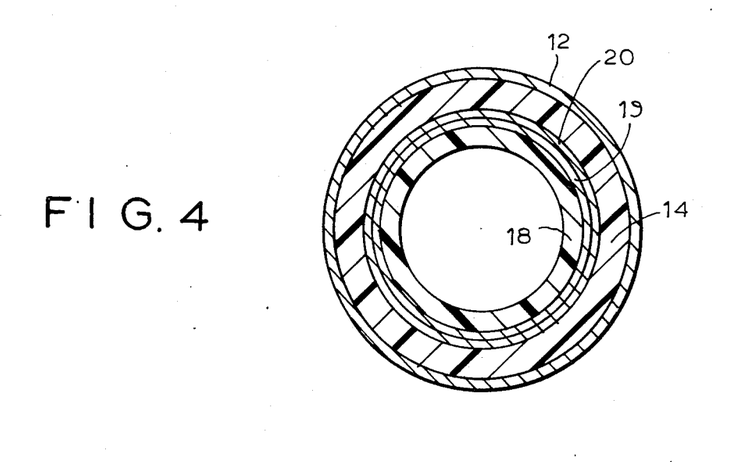
FIG. 4 is a cross-sectional view taken along the line 4—4 of FIG. 3.

As best seen in FIGS. 3 and 4, the section of wall 12 which is captured between tubular members 14 and 18 consists of a section 19 which is affixed to the exterior surface of tubular member 18 and section 20, which extends between the end of clamping member 14 and the end of connector member 18. After insertion of connector member 18, sections 19 and 20 of wall 12 are in substantially side-by-side relation and held in tight frictional engagement therebetween by the force exerted by the deformed member.

Figure 5:
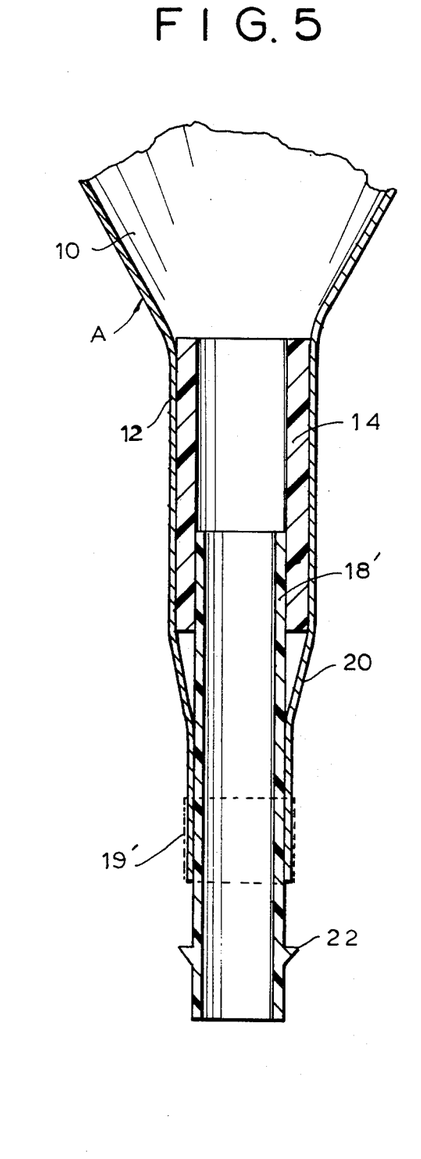
FIG. 5 is a side cross-sectional view of a second preferred embodiment of the present invention, shown prior to the insertion step.
Figure 6:
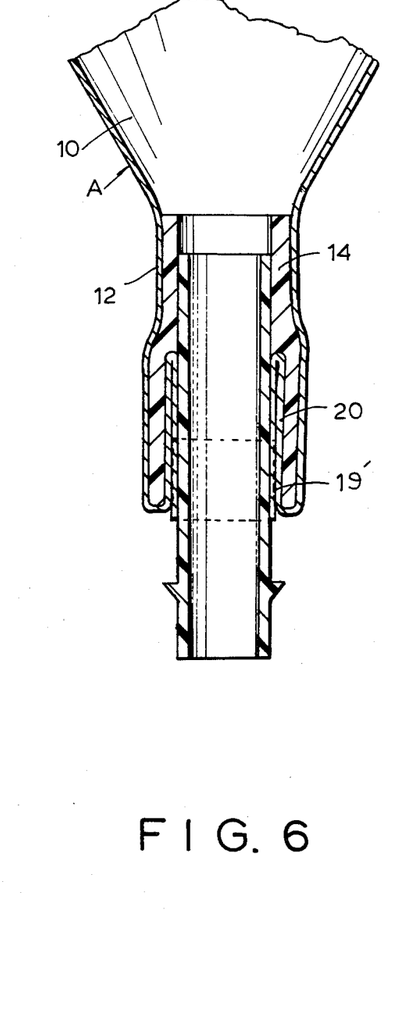
FIG. 6 is a side cross-sectional view similar to the second preferred embodiment illustrated in FIG. 5, shown subsequent to the insertion step.

FIGS. 5 and 6 illustrate a second preferred embodiment of the present invention. In this embodiment, tubular clamping member 18' is longer in length than clamping member 18 of the first embodiment. A section of member 18' is situated within connector member 14 in its initial position. Member 18' is adhesively affixed to the interior surface of wall 12 by welding or adhesive, as in the first embodiment. In this embodiment, a portion 19' of the exterior surface of the wall 12 is coated with a layer of adhesive prior to insertion of member 18' fully within member 14.

When connector member 18' is fully inserted within tubular member 14, as seen in FIG. 6, the end thereof extends into member 14 beyond the section of wall 12 captured therebetween. The adhesive-coated section 19' of wall 12 is captured between the tubular members 14 and 18', facing a second portion 20 of wall 12. In this manner, section 19' of wall 12 is adhesively sealed to section 20.

The second preferred embodiment has an advantage over the embodiment shown in FIGS. 1-4 in that the tubular members may be handled as a unit as a section of the clamping member 18' is situated within connector member 14 before insertion into the port section of the container. In addition, the layer of adhesive on portion 19' improves the seal.

The free or unattached end of connector member 18' of the second preferred embodiment is preferably provided with an outwardly extending annular protrusion or flange 22. Flange 22 may be used to connect a tube or other external member to the end of member 18' and, thus, to the port section of the container.

Figure 7:
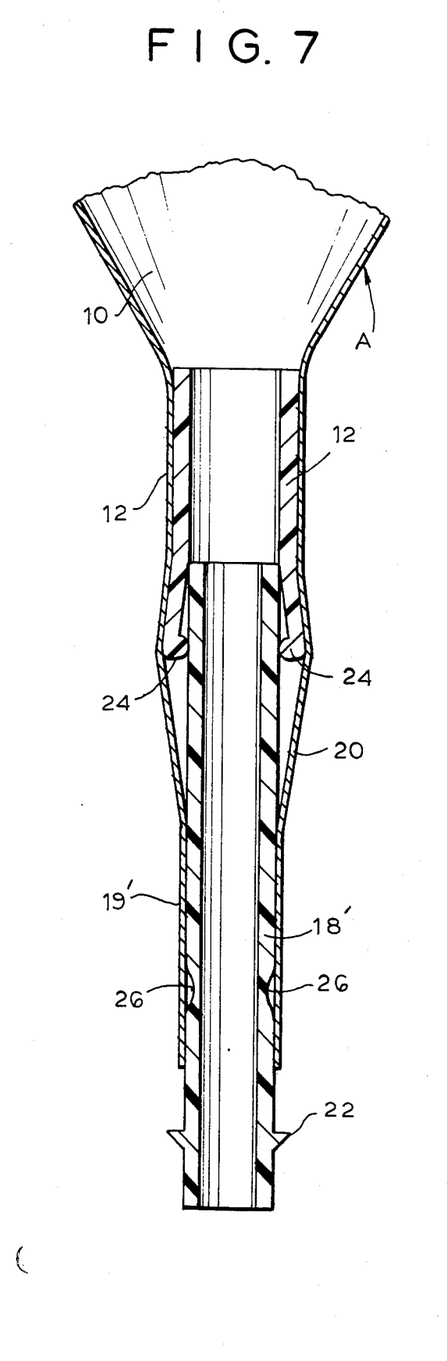
FIG. 7 is a cross-sectional view of a third preferred embodiment of the present invention, shown prior to the insertion step.
Figure 8:
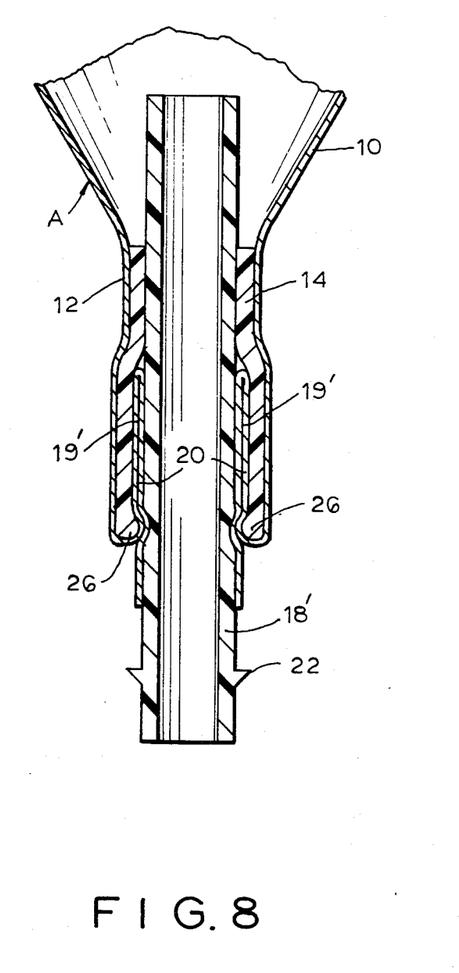
FIG. 8 is a cross-sectional view of the third preferred embodiment illustrated in FIG. 7, shown subsequent to the insertion step.

FIGS. 7 and 8 show a third preferred embodiment of the present invention. The third embodiment is quite similar to the second embodiment, with the exception that detent means are provided to enhance and strengthen the seal created. In this instance, the interior section of clamping member 14 adjacent to the end thereof is provided with a detent means in the form of an annular protrusion 24. When the connector member 18' is inserted within the clamping member 14, annular protrusion 24 aligns with annular recess 26 in the surface of member 18', as shown in FIG. 8, such that portions of wall sections 19' and 20 of wall 12 are captured therebetween in a sealing manner.

Figure 9:
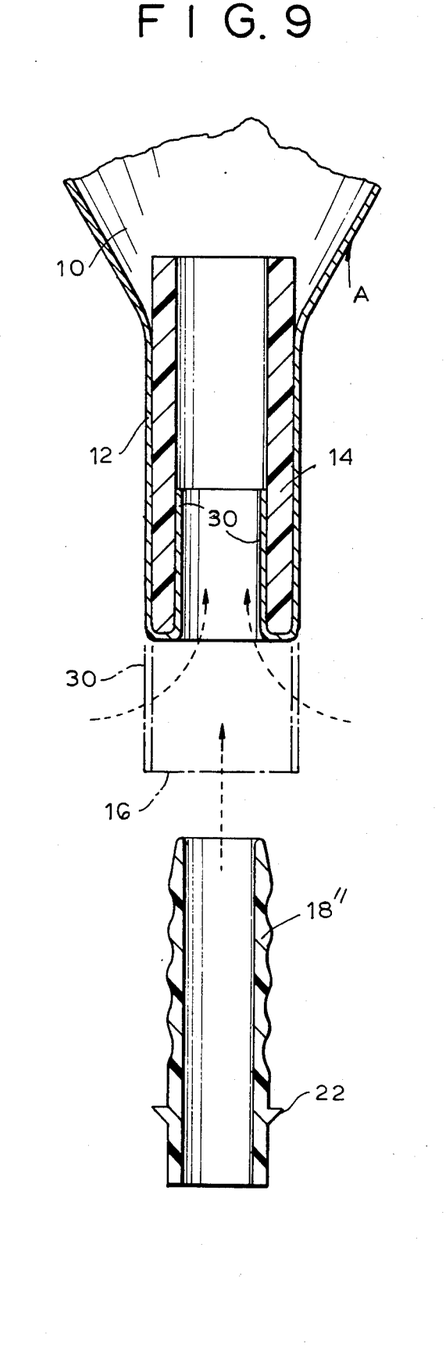
FIG. 9 is a cross-sectional view of a fourth preferred embodiment of the present invention, shown prior to the insertion step.
Figure 10:
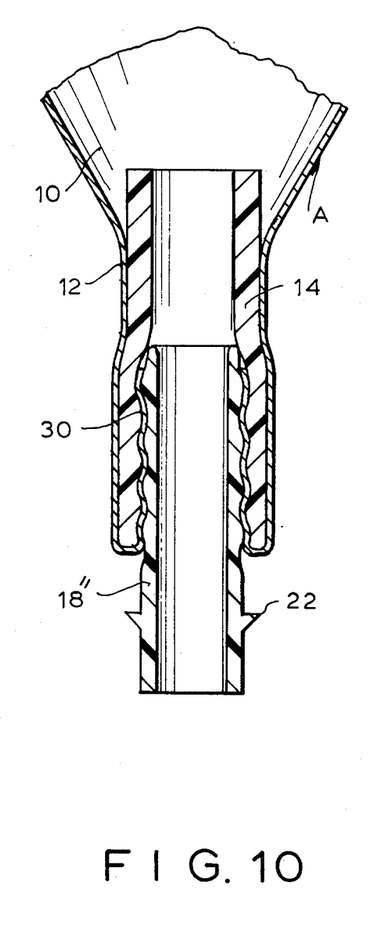
FIG. 10 is a cross-sectional view of the fourth preferred embodiment illustrated in FIG. 9, shown subsequent to the insertion step.

FIGS. 9 and 10 illustrate a fourth preferred embodiment of the present invention wherein tubular connector member 18'' is not initially located within wall 12, but is remote from wall 12 prior to insertion into clamping member 14. In this case, clamping member 14 is first located within wall 12 at a distance from the end 16 thereof. The end section 30 of wall 12 is then folded into the interior of tubular member 14, as illustrated in FIG. 9. Thereafter, connector means 18''', having an irregular exterior surface, is forceably inserted within the interior of clamping member 14 such that section 30 of wall 12 is sealingly engaged therebetween, as shown in FIG. 10.

Figure 11:
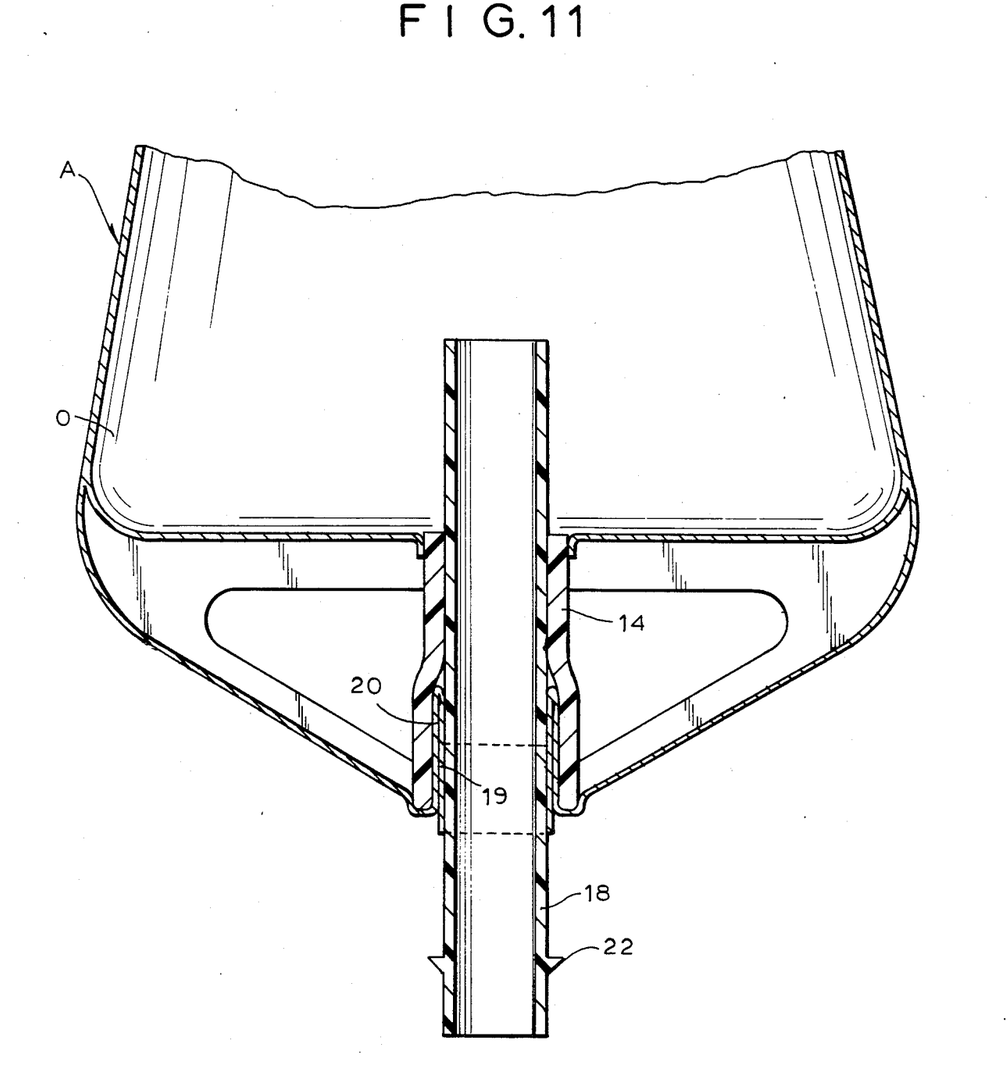
FIG. 11 is a side cross-sectional view of a typical embodiment of the present invention wherein the connector tube is elongated to create a sump.

FIG. 11 illustrates a portion of a fluid container A with the reservoir section 10 and a port section including a generally cylindrical wall 12. Clamping member 14 is lodged within wall 12. Connector member 18 is welded or glued to section 19 of wall 12. Section 19, along with section 20, are captured between the tubular members to provide a seal. The embodiment shown in FIG. 11 differes from the first, second and fourth preferred embodiments of the present invention in that tubular connector member 18 is elongated enough so that the inner end thereof is substantially above the end of clamping member 14 so as to create a sump at the bottom of container A.

It should now be appreciated that the connector member can be mounted to the elongated port section of a container in a simple and economical manner in accordance with the present invention. By providing the necessary connecting means, such as an annular protrusion 22 on the exposed exterior surface of connector member, flexible tubes, drain valves and the like can be easily affixed to the container port. The mounting of the present invention does not require accurate welding or complete adhesive sealing in order to achieve a fluid-tight seal. Further, no specialized or expensive machinery is required, to provide a reliable attachment.

While only a limited number of preferred embodiments have been dislcosed herein for purposes of illustration, it is obvious that many variations and modifications could be made thereto. It is intended to cover all of these variations and modifications which fall within the scope of the present invention, as defined by the following claims.

We claim:

1. A fluid container comprising a fluid reservoir section and a port section extending from said reservoir section and formed of a relatively flexible, generally cylindrical wall having a longitudinally displaceable section, first tubular means situated within said wall, and having an outer diameter substantially equal to the inner diameter of said wall, second tubular means at least partially situated within said displaceable section in a manner which prevents substantial relative movement therebetween, one of said means being substantially non-elastic and the other said means being relatively elastic, a portion of said second tubular means being inserted within said first tubular means, a section of said wall being sealingly engaged between the exterior surface tubular means and the inner surface of said first tubular means.

2. The container of claim 1, wherein said wall section comprises first and second substantially side-by-side portions.

3. The container of claim 2, wherein one of said portions is welded to said exterior surface of said second tubular means.

4. The container of claim 2, wherein one of said portions is adhesively sealed to said exterior of said second tubular means.

5. The container of claim 1, wherein said second tubular means comprises a relatively rigid tube section.

6. The container of claim 1, wherein said first tubular means comprises a heat shrinkable material.

7. The container of claim 1, wherein said first tubular means comprises an interior layer of hot melt material.

8. The container of claim 1, further comprising detent means on one of said further means and detent receiving means on the other of said tubular means.

9. The container of claim 1, further comprising annular protrusion means on one of said tubular means and annual protrusion receiving means on the other of said tubular means.

10. A connector for mounting in a fluid container or the like of the type having a reservoir section and a port section extending from said reservoir section, said port section comprising a relatively flexible, generally cylindrical wall, said connector comprising a first tubular member and a second tubular member situated within said wall, said second tubular member being received within said wall in a manner which prevents substantial relative movement therebetween, said wall extending over the exterior surface of and into said first member, a section of said wall extending along the interior surface of said first member, said second member being at least partially situated within said first member, with said section of said wall sealingly engaged between the exterior surface of said second member and the interior surface of said first member, one of said members being in a slighly deformed state.

11. The connector of claim 10, wherein said section comprises a first portion situated adjacent the interior surface of said first member and a second portion situated adjacent the exterior surface of said second member.

12. The connector of claim 11, further comprising means for affixing said second portion of said wall to the exterior surface of said second member.

13. The connector of claim 11, wherein said second member extends beyond the end of said first member.

14. The connector of claim 11, further comprising detent means on one of said members and detent receiving means on the other of said members.

15. The connector of claim 11, wherein said first member is relatively freely received within said wall.

16. The connector of claim 11, wherein said first tubular means comprises an interior layer of hot melt material.

17. A method for affixing a tubular connector member to the relatively flexible wall of the port section of a fluid container or the like, the method comprising the steps of: placing a tubular clamping member within the wall at a location spaced from the end thereof, and forceably inserting the connector member into the clamping member so as to deform one of the members, sealingly engaging a section of said wall between the interior surface of said clamping member and the exterior surface of said connector member.

18. The method of claim 17, further comprising the step of placing the connector member at least partially within the wall proximate the end thereof prior to inserting the connector member into the clamping member.

19. The method of claim 17, further comprising the step of affixing the exterior surface of the connector member to the wall prior to inserting same into the clamping member.

20. The method of claim 17, wherein the engaged section has two portions, one of the portions being affixed to the exterior surface of the connector member and the other of the portions being situated adjacent the interior surface of the clamping member.

21. The method of claim 17, wherein the clamping member comprises heat shrinkable material, and further comprising the step of heating said clamping member.

* * * * *